United States Patent [19]

Connell et al.

[11] Patent Number: 5,633,277
[45] Date of Patent: May 27, 1997

[54] SULFONAMIDE AMINOMETHYLENE DERIVATIVES AS IMMUNOSUPPRESSANTS

[75] Inventors: Richard D. Connell, New Haven; David G. Osterman, Glastonbury; Michael E. Katz, Wallingford; Robert D. Dally, Branford, all of Conn.

[73] Assignee: Miles Inc., West Haven, Conn.

[21] Appl. No.: 535,507

[22] Filed: Sep. 26, 1995

Related U.S. Application Data

[63] Continuation of Ser. No. 15,502, Feb. 9, 1993, abandoned.

[51] Int. Cl.$^6$ ............... A61K 3/40; C07D 207/00; C07D 405/02
[52] U.S. Cl. ............... 514/428; 514/411; 514/423; 548/526; 548/528; 548/532; 548/538; 548/568
[58] Field of Search ............... 548/526, 528, 548/532, 538, 568; 514/423, 411, 428

[56] References Cited

FOREIGN PATENT DOCUMENTS

| | | | |
|---|---|---|---|
| 2005337 | 12/1989 | Canada | A61K 37/00 |
| 352 000 | 1/1990 | European Pat. Off. | |
| 0361341 | 4/1990 | European Pat. Off. | C07K 5/02 |
| 0363284 | 4/1990 | European Pat. Off. | C07K 5/02 |
| 0374097 | 6/1990 | European Pat. Off. | C07K 5/02 |
| 374 756 | 6/1990 | European Pat. Off. | |
| 0387231 | 9/1990 | European Pat. Off. | C07K 7/02 |
| 3219113 | 11/1983 | Germany | |
| 9000399 | 1/1990 | WIPO | A61K 37/02 |

OTHER PUBLICATIONS

CA100(9):61785q (1983).

Poe et al., "Human Cytotoxic Lymphocyte Tryptase", The Journal of Biological Chemistry, 263(26):13215–13222 (1988).

Simon et al., "Purification and Characterization of a T cell specific serine proteinase (TSP–1) from cloned cytolytic T lymphocytes", The EMBO Journal, 5(12):3267–3274 (1986).

*Primary Examiner*—Shean C. Wu

[57] ABSTRACT

Compounds which suppress human T-lymphocyte proliferation are disclosed. The active compounds essentially contain at least the following structure:

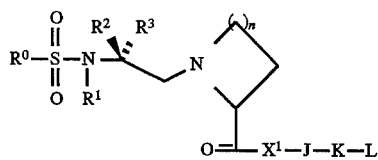

12 Claims, No Drawings

SULFONAMIDE AMINOMETHYLENE DERIVATIVES AS IMMUNOSUPPRESSANTS

This application is a continuation of application Ser. No. 08/015,502 filed on Feb. 9, 1993, now abandoned.

FIELD OF THE INVENTION

The invention relates to methods and compounds for controlling inflammatory processes in humans through mediation of inflammatory cell proliferation. More particularly, the present invention is a method for suppressing T-lymphocytes using a class of novel compounds.

BACKGROUND

Compounds which retard the production of cytokines such as interleukin-2 (IL-2) are known. For instance, U.S. Pat. No. 4,764,503 assigned to Sandoz Ltd., Basel, Switzerland, describes a compound generically referred to as Cyclosporin A (hereinafter referred to as "CsA"), and U.S. Pat. No. 4,894,366 assigned to Fujisawa Pharmaceuticals, Osaka, Japan, describes a compound they designate as "FKS06." Both CsA and FK 506 are claimed to inhibit IL-2 production and bind to cellular receptor proteins that possess Peptidyl Prolyl Isomerase (PPIase) activity (Johansson et al., 1990, Transplantation 50:10017).

It was initially postulated by those skilled in the art that the specific binding by such compounds to PPIase type proteins led to inhibition of the protein's isomerase activity which, in turn, led to inhibition of T-cell proliferation. Thus, these PPIase type proteins were referred to as "immunophilins", with the cellular receptor proteins that bound to CsA and FK506 being referred to as "cyclophilin" and "FKS06 binding protein", respectively. FK506 binding protein is also simply referred to as "FKBP" (Harding et al., 1989, Nature 341:758).

Recent publications report that the inhibition of PPIase activity, in and of itself, is not sufficient for immunosuppressant activity. However, there is support in the literature that inhibitory binding to PPIase-type enzymes probably contributes to ultimate T-cell suppression (Sigal et al. 1991, J. Exp. Med. 173:619).

This disclosure presents a new class of synthetic compounds that both suppress the proliferation of T-cells and inhibit the isomerase activity of the FKBP-type of PPIases.

CsA, a cyclic undecapeptide, has received FDA approval for use as an adjunct to organ transplant procedures. However, CsA is administered with caution due to its known toxicity. Currently, CsA is prescribed in situations where the risks of non treatment outweigh the risks of its therapeutic complications.

As a result, efforts to expand the application of CsA into non life threatening indications such as chronic maintenance of autoimmune disorders have been limited by the well-known side effects of this drug. The use of CsA leads to a variety of disorders including: nephrotoxicity, such as impairment of glomerular filtration and irreversible interstitial fibrosis (Kopp et al., 1991, J. Am. Soc. Nephrol. 1:162); neurological deficits, such as involuntary tremors, or non-specific cerebral angina such as non-localized headaches (De Groen et al, 1987, N. Engl. J. Med. 317:861); and vascular hypertension with complications resulting therefrom (Kahan et al., 1989, N. Engl. J. Med. 321:1725).

Recent efforts to investigate the cause of the adverse effects of CsA administration have centered on the role of CsA breakdown into toxic metabolites (Bowers et al., 1990, Clin. Chem. 36:1875; Burke et al., 1990, Transplantation 50:901). The prevailing thought is that CsA toxicity is due to such metabolites and not due to the nature of the CsA binding to the PPIase, cyclophilin (Akagi et al., 1991, J. Int. Med. Res. 19:1; Ryffel et al., 1988, Transplantation 46:905).

Thus, inhibitor compounds that do not resemble CsA structurally, yet bind to PPIases, should be more amenable to therapeutic applications. Such non-toxic immunosuppressors would benefit the art, especially for chronic administration such as required in the treatment of autoimmune disorders.

The compound FK506 is structurally different from CsA and does not produce the same type of toxic metabolites. FK506 has been shown to be effective in some transplant patients who do not respond to CsA (Tucci et al., 1989, J. Immunol. 143:718).

However, testing of FK506 in humans was delayed due to severe vasculitis observed in treatment regimens in dogs and baboons (Collier et al., 1988, Transplant Proc. 20:226). Furthermore, other clinical side effects and complications of FK506 administration are being reported (Frayha et al., 1991, Lancet 337:296; Kitahara et al., 1991, Lancet 337:1234). It has also been reported that "overall, the absolute rate of clinical rejection in FK506 [post-organ transplantation] patients is only slightly lower than with current standard therapies" (Holechek, 1991, Anna. J. 18:199).

In an attempt to alleviate the FK506 side effects, many minor modifications to the base structure have been reported. For example, U.S. Pat. No. 5,057,608 assigned to Merck & Co. and WIPO Publication No. W089/05304 assigned to FISONS PLC Inc. both disclose chemical variations of the FKS06 compound.

To date only a few studies on the metabolism of FK506 have been published, and little information has been reported on the toxicity of its metabolites (Johansson et al., 1990, Transplantation 50:1001; Christians et al., 1991, Clinical Biochemistry 24:271; Lhoest et al., 1991, Pharmaceutica Acta Helveticae 66:302). Since it is likely that the patterns of metabolism of the FK506 analogs and derivatives are similar to the parent compound, it is also likely that many of the side effects of FK506 will be shared by the derivatives.

As is true for CsA, the toxicity of FK506 is postulated to be based on its structure and not due to its binding activity with the immunophilin FKBP. It is further postulated that the toxicities of compounds such as CsA and FK506 are due to various chemical groups found in these structures which do not participate in the immunosuppressive activity, such as those groups which result in the toxic metabolites of CsA bio-processing. Thus, relatively compact molecules which do not resemble either CsA or FK506, and which have both immuno-suppressive and PPIase binding activity should be free of side effects associated with CsA and FK506.

The present invention presents a novel class of synthetic inhibitor compounds. The novel class includes synthetic aminomethylene derivatives that bind to human FKBP-type PPIases and demonstrate human peripheral T-lymphocyte inhibitory activity.

Amino-methylene derivatives are known. For example, several claimed amino-methylene HIV inhibitors have been published, including WO 90/00399 assigned to Smithkline Beckman Corp., EP 0387231 assigned to Washington University, and EP 0361341 assigned to Miles Inc., by assignment from Molecular Therapeutics, Inc. Similarily, amino-methylene inhibitors of the enzyme renin have also been published, including EP 0374097 assigned to CIBA Geigy AG. Also published are amino methylene compounds which are claimed to be therapeutics for neurologic dysfunctions such as EP 374,756 assigned to Merck Inc.

As used herein, the term "aminomethylene-prolyl spacer" refers to a peptide fragment in which the carbonyl of the central amide bond has been replaced by an alkyl fragment such as a methylene group.

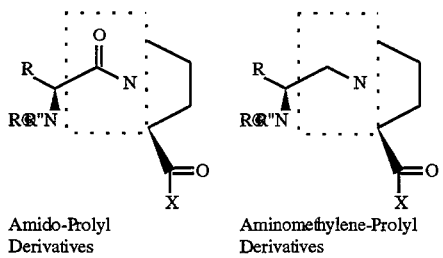

Amido-Prolyl Derivatives

Aminomethylene-Prolyl Derivatives (I)

It is therefore an object of the present invention to provide for compounds and compositions containing such aminomethylene derivatives for suppression of pathological and abnormal human peripheral T-lymphocyte proliferation.

It is also an object of the present invention to provide a novel class of compounds suitable for therapeutic compositions designed to suppress pathological immune responses, such as the hyperimmune response in organ transplantation rejection, the self-destructive autoimmune diseases, and the overproduction and excessive proliferation of immune cells such as in infectious disease states.

More specific objects include provisions for compounds, compositions and methods for treatment and prevention of rejection of transplanted organs or tissues such as kidney, heart, lung, liver, bone marrow, skin grafts, and corneal replacement.

It is a further object to provide compounds, compositions and methods for use in the treatment of autoimmune, degenerative, inflammatory, proliferative and hyperproliferative diseases, such as rheumatoid arthritis, osteoarthritis, other degenerative joint diseases, joint inflammation such as associated with infectious diseases such as suppurative arthritis, and secondary arthritis such as those associated with gout, hemochromatosis, rheumatic fever, Sjörgens syndrome and tuberculosis.

Another object is to provide compounds, compositions and methods for use in the treatment of lupus erythematosus, systemic lupus erythematosus, Hashimoto's thyroiditis, multiple sclerosis, myasthenia gravis, type 1 diabetes, uveitis, nephrotic syndrome, and of cutaneous manifestations of immunologically-mediated diseases such as psoriasis, atopic dermatitis, contact dermatitis, eczematous dermatitides, seborrheic dermatitis, lichen planus, pemphigus, bollous pemphigoid, epidermolysis bullosa, urticaria, angioedemas, vasculitides, erythemas, cutaneous eosinophilias, and alopecia areata.

Yet another object is to provide compounds, compositions and methods for use in the treatment of abnormal T-cell proliferation such as lymphocytic leukemia; Hodgkin's disease, especially those subtypes involving abnormal T-cell subpopulations; non-Hodgkin's lymphomas, such as mycosis fungoides, convulated lymphocytic lymphoma, and immunoblastic sarcoma; and chronic lymphadenitis.

The above lists are non-limiting, and one skilled in the art could easily adapt the compounds, compositions and methods of the present invention to other indications, such adaptations being within the spirit and scope of the invention which will be described hereinbelow.

SUMMARY OF THE INVENTION

The presently claimed invention relates to active compounds of the following generalized structure:

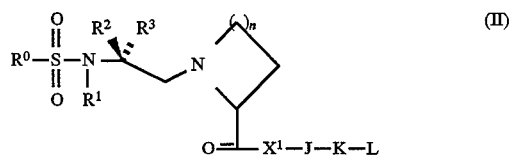

where $R^0$ is straight or branched alkyl (C1–C10), cycloalkyl (C3–C10), bicycloalkyl (C5–C12), tricycloalkyl (C7–C14), or tetracycloalkyl (C9–C16). These alkyl derivatives may be substituted by a doubly bonded oxygen atom in such a way as to form a ketone. These alkyl derivatives may also be substituted by straight or branched alkoxy (C1–C3), cyano, carboalkoxy (with straight or branched alkoxy of C1–C6), alkylsulfonyl (C1–C5), or up to three times by fluoro. $R^0$ may also be an quinolyl, styryl, or aryl. Throughout this application, aryl refers to phenyl derivatives such as phenyl, napthyl, and related aromatic, carbon derivatives. These aryl derivatives may be substituted up to three fold by straight or branched alkyl (C1–C6). $R^0$ may also be heteroaryl (six membered with up to 2 nitrogens), or a 5-membered ring heterocycle such as furan, thiophene, 1,3-thiazole; these heterocycles may be substituted by an acetylamino or a five membered ring heterocycle containing nitrogen or oxygen or both.

$R^1$ is hydrogen or methyl.

$R^2$ and $R^3$ are defined as follows: one of $R^2$ and $R^3$ is hydrogen and the other is straight or branched alkyl (C1–C6) that may be substituted by cycloalkyl (C6), hydroxy, straight or branched alkoxy (C1–C4), benzyloxy, or aryl. The aryl may be substituted by hydroxy or methoxy.

n=an integer of 1, 2 or 3.

$X^1$ is oxygen or $NR^4$, where $R^4$ is hydrogen or methyl.

J is the divalent fragment

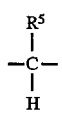

where $R^5$ is hydrogen, straight or branched alkyl (C1–C8). These alkyl derivatives could be substituted by hydroxy, straight or branched alkoxy (C1–C6), benzyloxy, cycloalkyl (C6), or phenyl.

K is one of the fragments

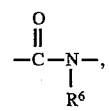

—HC=CH— or —(CH$_2$)$_p$— where $R^6$ is hydrogen or methyl and where it is understood that the carbonyl group is attached to "J" and that $NR^6$ is connected to "L", respectively, p=an integer of 1, 2, 3 or 4.

L is hydrogen, aryl, straight or branched alkyl (C1–C8) that may be substituted by aryl. The aryl group may be substituted by alkoxy (C1–C5), hydroxy, or amino. These aminoaryl derivatives may be substituted by straight or branched alkyl (C1–C6) or acetyl or both.

Included within the scope of the present invention are pharmacuetically acceptable salts of the above mentioned compounds. Pharmaceutically acceptable salts can be derived from mineral acids, carboxylic acids or sulfur containing acids, preferably from hydrochloric acid, hydrobromic acid, sulfuric acid, methane sulfonic acid, ethane sulfonic acid, toluene sulfonic acid, benzene sulfonic acid, naphthalene disulfonic acid, acetic acid, propionic acid, lactic acid, tartaric acid, citric acid, fumaric acid, maleic acid or benzoic acid. Most preferred are the hydrochlorides.

In the case of the present compounds being carboxylic acids or containing acidic functional groups, the invention includes metal salts and ammonium salts. Preferred are sodium, potassium or ammonium salts. The compounds of this invention exist as stereoisomeric forms, which either behave like image and mirror image (enantiomers) or not (diastereomers). Included within the scope of the invention are the enantiomers, the racemic forms and diastereomeric mixtures. Enantiomers as well as diastereomers can be separated by methods known to those skilled in the art (See E. L. Eliel, Stereochemistry of Carbon Compounds, McGraw Hill, 1962).

The presently claimed invention also relates to active compounds of the following generalized structure:

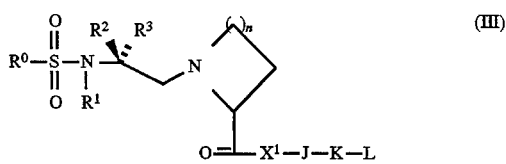

(III)

where $R^o$ is straight or branched alkyl (C1–C8), cycloalkyl (C3–C8), bicycloalkyl (C5–C10), tricycloalkyl (C7–C 12 ), or tetracycloalkyl (C9–C14). These alkyl derivatives may be substituted by a doubly bonded oxygen atom in such a way as to form a ketone. These alkyl derivatives may also be substituted by fluoro, methoxy, cyano, carboalkoxy (with straight or branched alkoxy of C1–C4), or an alkylsulfonyl (C1–C4). $R^o$ may also be an 8-quinolyl, styryl, aryl, or aryl that may be substituted up to three fold by straight or branched alkyl (C1–C6). $R^o$ may also be heteroaryl (six membered with up to 2 nitrogens), or a 5-membered ring heterocycle such as furan, thiophene, 1,3-thiazole; these heterocycles may be substituted by an acetylamino or a five membered ring heterocycle containing nitrogen or oxygen or both.

$R^1$ is hydrogen or methyl.

$R^2$ and $R^3$ are defined as follows: one of $R^2$ and $R^3$ is hydrogen and the other is straight or branched alkyl (C1–C6) that may be substituted by cycloalkyl (C6) or phenyl.

n=an integer of 1, 2 or 3.

$X^1$ is oxygen or $NR^4$, where $R^4$ is hydrogen or methyl.

J is the divalent fragment

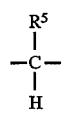

where $R^5$ is hydrogen, straight or branched alkyl (C1–C6). These derivatives could be substituted by hydroxy, alkoxy (C1–C6), benzyloxy, cycloalkyl (C6), or phenyl.

K is one of the fragments

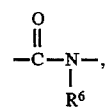

—HC=CH— or —(CH$_2$)$_p$— where $R^6$ is hydrogen or methyl and where it is understood that the carbonyl group is attached to "J" and that $NR^6$ is connected to "L", respectively, p=an integer of 2 or 3.

L is hydrogen, aryl, straight or branched alkyl (C1–C6) that may be substituted by aryl. The aryl group may be substituted by alkoxy (C1–C5), hydroxy, or amino. These aminoaryl derivatives may be substituted by alkyl (C1–C4) or acetyl or both.

Included within the scope of the present invention are pharmacuetically acceptable salts of the above mentioned compounds. Pharmaceutically acceptable salts can be derived from mineral acids, carboxylic acids or sulfur-containing acids, preferably from hydrochloric acid, hydrobromic acid, sulfuric acid, methane sulfonic acid, ethane sulfonic acid, toluene sulfonic acid, benzene sulfonic acid, naphthalene disulfonic acid, acetic acid, propionic acid, lactic acid, tartaric acid, citric acid, fumaric acid, maleic acid or benzoic acid. Most preferred are the hydrochlorides.

Preferred compounds of the present invention have the following generalized structure:

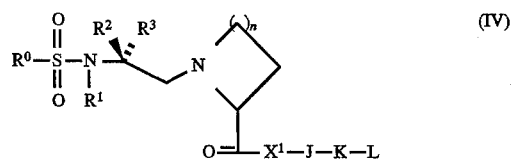

(IV)

where $R^o$ is straight or branched alkyl (C1–C6). These alkyl derivatives may be substituted by a methylsulfonyl. $R^o$ may also be styryl or a tricycloalkyl of C10, substituted by a doubly bonded oxygen atom in such a way as to form a ketone. $R^o$ may also be an 8-quinolyl, aryl, or aryl that may be substituted up to three fold by straight or branched alkyl (C1–C3). $R^o$ may also be heteroaryl (six membered with 1 nitrogen), or a 5-membered ring heterocycle such as furan, thiophene, 1,3-thiazole; these heterocycles may be substituted by an acetylamino or an isoxazol-3-yl.

$R^1$ is hydrogen.

$R^2$ and $R^3$ are defined as follows: one of $R^2$ and $R^3$ is hydrogen and the other is straight or branched alkyl (C1–C4) that may be substituted by cycloalkyl (C6).

n=an integer of 1, 2 or 3.

$X^1$ is oxygen or $NR^4$, where $R^4$ is hydrogen.

J is the divalent fragment

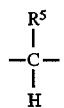

where $R^5$ is hydrogen, straight or branched alkyl (C1–C4).

K is one of the fragments

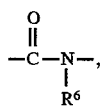

—HC=CH— or —(CH$_2$)$_p$—
where R$^6$ is hydrogen and where it is understood that the carbonyl group is attached to "J" and that NR$^6$ is connected to "L", respectively.
p=an integer of 2.
L is hydrogen, phenyl, straight or branched alkyl (C1–C3) that may be substituted by aryl.

Included within the scope of the present invention are pharmacuetically acceptable salts of the above mentioned compounds. Most preferred are the hydrochlorides.

Preferred Method of Synthesis

Synthesis of Dipeptide Derivatives

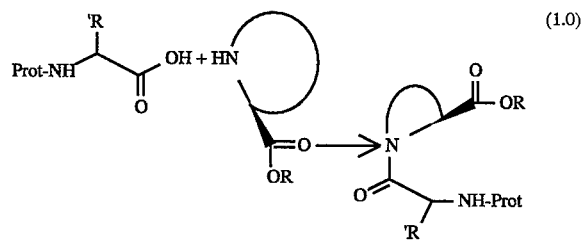

Prot = protecting group

Imino acid derivatives could be dehydratively coupled to N-protected, amino acid derivatives using standard coupling agents such as PPA, DCC or other reagents as described in standard books on peptide coupling (such as Bodanszky et al. The Practice of Peptide Synthesis: Springer-Verlag, Vol 21, 1984). The group used to protect the nitrogen of these amino acids could be either carbotertbutoxy, carbobenzyloxy, carboallyloxy, or other temporary protecting groups as described in the literature (T. W. Greene et al, Protective Groups in Organic Synthesis, 2nd Edition; John Wiley & Sons, 1991).

Synthesis of Aminomethylenes

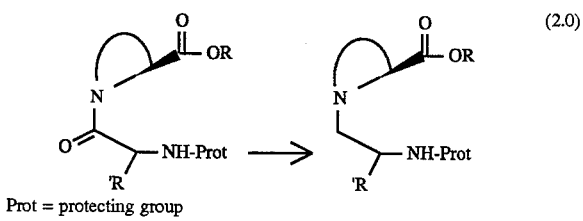

Prot = protecting group

A convenient route to prepare the present compounds involves reduction of the central peptide bond as depicted in equation 2.0. Standard methods to effect transformations of this type have been reported (Cushman, M. et al. *J. Org. Chem.* 1991, 56, 4161–7). For example, the intermediate amide bond can be reduced with a borohydride reagent such as borane in a polar solvent such as tetrahydrofuran, ether, or dimethoxyethane.

Alternatively, these derivatives may also be prepared by a procedure in which the amide bond is first converted to a thioamide intermediate using sulfur transfer reagents such as Lawesson's Reagent (Synthesis 1979, 941). The resulting thioamide obtained by this or other procedures may be reduced to the corresponding aminomethylene derivative by treatment with a reducing reagent such as Raney nickel. In cases where the thioamide derivative is a phenylmethyl ester derivative, reduction of the thioamide may lead directly to the corresponding reduced derivative containing a free carboxylic acid group (Eq. 2.1)

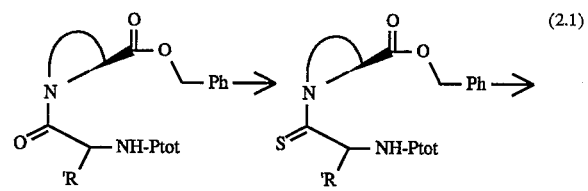

Formation of Aminomethylene Carboxylic Acids.

Prot = protecting group

Although methods as depicted in Eq. 2.1 may allow for the formation of carboxylic acid derivatives directly from the corresponding thioamide phenylmethyl esters, these intermedates are also obtained from the corresponding esters (Eq. 3). Conditions used to effect hydrolysis or conversion of ester derivatives to acid derivatives are described in detail in the literature (T. W. Greene et al, Protective Groups in Organic Synthesis, 2nd Edition; John Wiley & Sons, 1991).

C-Terminal Homologation of Aminomethylenes

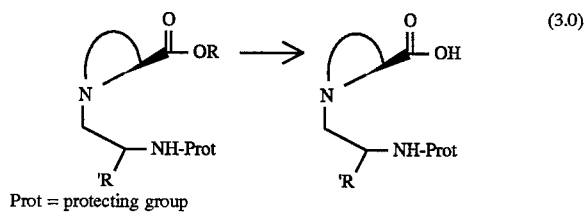

Prot = protecting group

Aminomethylene-carboxylic acid derivatives prepared as shown in Eq. 2.1, Eq. 3.0, or by other methods can be dehydratively coupled to a variety of alcohol or amines to provide the corresponding ester (X=O) or amide derivatives (X=NR). This dehydrative coupling can be achieved with standard coupling agents such as PPA, DCC or other reagents as described in standard books on peptide coupling (such as Bodanszky The Practice of Peptide Synthesis: Springer-Verlag, Vol 21, 1984).

Deprotection of Aminomethylene N-Termini

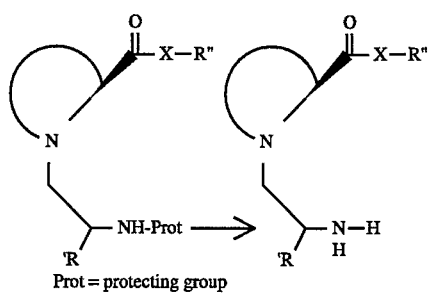

(5.0)

Prot = protecting group

The deprotection of amine derivatives has been described (T. W. Greene et al, Protective Groups in Organic Synthesis, 2nd Edition; John Wiley & Sons, 1991). These methods are useful for the conversion of protected amine derivatives to free amino derivatives.

Formation of Sulfonamides

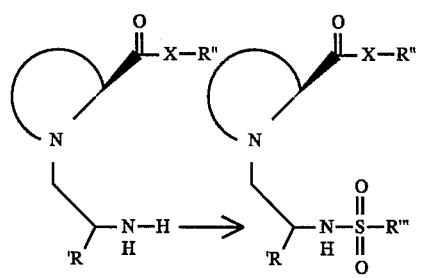

(6.0)

Amine derivatives prepared using methods illustrated by Eq. 5.0 or from other sources may be treated with sulfonyl halides in halogenated solvents such as dichloromethane, 1,2-dichloroethane or chloroform to form the corresponding sulfonamides.

Alternatively, sulfonamide derivatives may be prepared in opening N-protected aziridine derivatives as shown in Eq. 7.0.

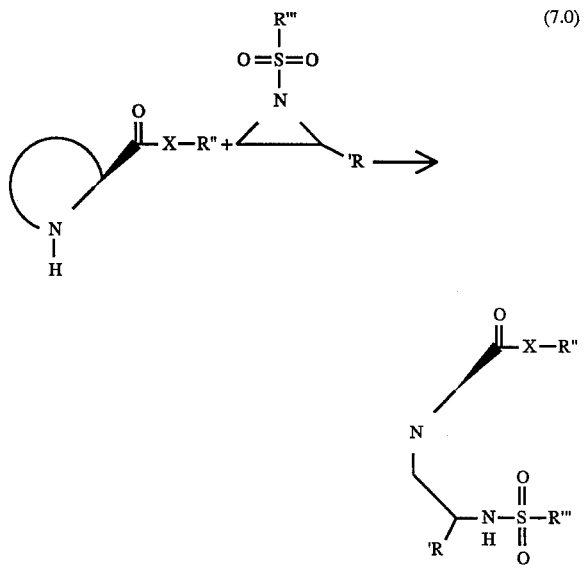

(7.0)

The presently claimed compounds were found to be effective at low micromolar doses in both in vivo assays for inhibition of mitogen-induced human T-cell proliferation and NF-AT directed β-galactosidase expression. Moreover, the results from the rat adjuvant arthritis model (described in detail further below) indicate that the present class of compounds exhibits desirable biological properties (prophylactic prevention of paw swelling), at the concentration tested (10 mg/kg/dose).

The present invention encompasses pharmaceutical formulations which, in addition to non-toxic, inert pharmaceutically suitable excipients, contain the compounds of the invention.

The present invention also includes pharmaceutical formulations in dosage units. This means that the formulations are present in the form of individual part, for example, tablets, dragees, capsules, caplets, pills, suppositories and ampules, the active compound content of which corresponds to a fraction or a multiple of an individual dose. The dosage units can contain, for example, 1, 2, 3 or 4 individual doses; or ½, ⅓ or ¼ of an individual dose. An individual dose preferably contains the amount of active compound which is given in one administration and which usually corresponds to a whole, one half, one third or one quarter of a daily dose.

By non-toxic inert pharmaceutically suitable excipients there are to be understood solid, semi-solid or liquid diluents, fillers and formulation auxiliaries of all types.

Preferred pharmaceutical formulations which may be mentioned are tablets, dragees, capsules, caplets, pills, granules, suppositories, solutions, suspensions and emulsions, paste, ointments, glues, creams, lotions, dusting powders and sprays. Tablets, dragees, capsules, caplets, pills and granules can contain the active compounds in addition to the customary excipients, such as (a) fillers and extenders, for example, starches, lactose, sucrose, glucose, mannitol and silicic acid, (b) binders, for example, carboxymethylcellulose, alginates, gelatin and polyvinylpyrrolidone, (c) humectants, for example, glycerol, (d) disintegrating agents, for example, agar-agar, calcium carbonate and sodium carbonate, (e) solution retarders, for example, paraffin and (f) absorption accelerators, for example, quaternary ammonium compounds, (g) wetting agents, for example, cetyl alcohol and glycerol monostearate, (h) absorbents, for example, kaolin and bentonite and (i) lubricants, for example, talc, calcium stearate, magnesium stearate and solid polyethylene glycols, or mixtures of the substances listed under (a) to (i) directly hereinabove.

The tablets, dragees, capsules, caplets, pills and granules can be provided with the customary coatings and shells, optionally containing opacifying agents and can also be of such composition that they release the active compounds only or preferentially in a certain part of the intestinal tract, optionally in a delayed manner. Examples of embedding compositions which can be used are polymeric substances and waxes.

The active compounds can also be present in microencapsulated form, if appropriate with one or more of the abovementioned excipients. Suppositories can contain, in addition to the active compounds, the customary water-soluble or water-insoluble excipients, for example, polyethylene glycols, fats, for example, cacao fat and higher esters (for example, C 14 -alcohol with C16 -fatty acid), or mixtures of these substances.

Ointments, pastes, creams and gels can contain, in addition to the active compounds, the customary excipients, for example, animal and vegetable fats, waxes, paraffins, starch tragacanth, cellulose derivatives, polyethylene glycols, silicones, bentonites, silicic acid, talc and zinc oxide, or mixtures of these substances.

Dusting powders and sprays can contain, in addition to the active compounds, the customary excipients, for example, lactose, talc, silicic acid, aluminum hydroxide, calcium silicate and polyamide powder, or mixtures of these substances. Sprays can additionally contain customary propellants, for example, chlorofluorohydrocarbons.

Solutions and emulsions can contain, in addition to the active compounds, customary excipients, such as solvents, solubilizing agents and emulsifiers, for example, water, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil and sesame oil, glycerol, glycerol formal, tetrahydrofurfuryl alcohol, polyethylene glycols and fatty acid esters of sorbitan, or mixtures of these substances.

For parenteral administration, the solutions and emulsions can also be in a sterile form which is isotonic with blood. Suspensions can contain, in addition to the active compounds, customary excipients, such as liquid diluents, for example, water, ethyl alcohol or propylene glycol and suspending agents, for example, ethoxylated isostearyl alcohols, polyoxyethylene sorbitol and sorbitan esters, microcrystalline cellulose, aluminum methydroxide, bentonite, agar-agar, and tragacanth, or mixtures of these substances.

The abovementioned pharmaceutical formulations can also contain other pharmaceutical active compounds in addition to the claimed compounds of the present invention.

The aforementioned pharmaceutical formulations are prepared in the customary manner by known methods, for example, by mixing the active compound or compounds with the excipient or excipients.

The formulations mentioned can be used either with humans and animals, orally, rectally, bucally, parenterally (intra-venously, intramuscularly or subcutaneously), intracisternally, intravaginally, intraperitoneally or locally (dusting powder, ointment or drops) and for the therapy of infection in hollow spaces or body cavities. Suitable formulations are injection solutions, solutions and suspensions for oral therapy, gels, pour-on formulations, emulsions, ointments or drops. Ophthalmological and dermatological formulations, silver salts and other salts, ear drops, eye ointments, powders or solutions can be used for local therapy.

It is furthermore possible to use gels, powders, dusting powders, tablets, sustained release tablets, premixes, concentrates, granules, pellets, capsules, caplets, aerosols, sprays and inhalates on humans and animals. The compounds according to the invention can furthermore be incorporated into other carrier materials, such as, for example, plastics (e.g., chains of plastic for local therapy), collagen or bone cement.

DETAILED DESCRIPTION

The following describes a preferred way to prepare the compounds of the present invention.

REAGENTS AND INSTRUMENTS:

Anhydrous tetrahydrofuran (THF), ethyl ether (Et$_2$O), and acetonitrile were distilled from calcium hydride prior to use. Unless otherwise stated, all reagents discussed in the following examples were commercially available from Aldrich Chemical Co, Milwakee, Wis., or Janssen Chimica through the U.S. vender Spectrum Chemicals Mfg. Corp., New Brunswick, N.J.

All reactions were carried out in oven-dried glassware (140° C.) which were cooled under argon prior to use. Crude products were purified by flash column chromatography using 230–400 mesh silica gel (35–70 um) or medium/high pressure liquid chromatography using Shimadzu LC-8A Preparative liquid chromatography system equipped with columns packed with either 20 um or 10 um silica. Thin layer chromatography (TLC) was performed on aluminum-backed silica gel plates, and visualization was accomplished with a UV light or an iodine vapor chamber.

Proton ($^1$H) nuclear magnetic resonance (NMR) spectra were obtained on a GN-OMEGA-300 spectrometer at 300 MHz. Carbon ($^{13}$C) NMR were obtained on the same spectrometer at 75 MHz. Mass spectral data were obtained on a Kratos-MS 80RFA spectrometer using electron impact ionization (EI), chemical ionization (CI), or fast atom bombardment (FAB). Other mass spectral (MS) data were obtained on a Kratos CONCEPT I-H spectrometer, using liquid-cesium secondary ion (LSI) technique, a more modern version of fast atom bombardment (FAB).

Melting points were obtained on a Thomas Hoover capillary melting point apparatus in open-ended capillaries and are not corrected.

Abbreviations used in the following experimental section refer to the following reagents: DCC is 1,3-dicyclohexyl carbodiimide; DMAP is 4-dimethylaminopyridine; TFA is trifluoroacetic acid; HOBT is 1-hydroxybenzotriazole monohydrate.

Amino acid derivatives described as 1-[X]-L-Isoleucine are meant to signify a derivative of the the L-isomer of the amino acid Isoleucine, in which the α-amino group is attached to the the fragment X. In a similiar fashion, 1-[1-[X]-L-Proline]-L-Isoleucine is meant to represent a fragment that can be represented graphically as:

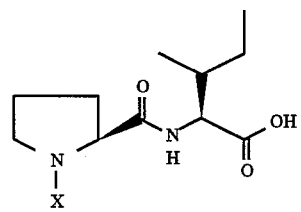

Example 1

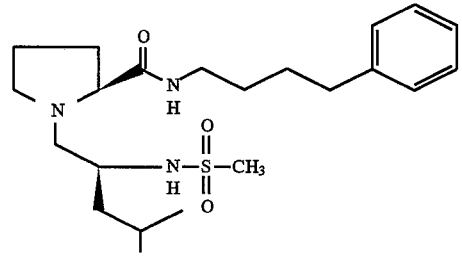

1- [2-(S)-Methanesulfonylamino-4-methylpentyl]-L-proline 4-Phenylbutylamide.

a) 1-Thio-1-[2-(S)-[[(1,1 -dimethylethoxy)carbonyl] amino]-4-methylpentyl]-L-Proline Benzyl Ester. This compound was prepared from in 49% yield using the procedure described earlier (*Synthesis*, 1979, 941). The $^1$H NMR of this compound was consistent with the structure. Rf=0.61 (2% methanol in dichloromethane).

b) 1-[2-(S)-[[(1,1-dimethylethoxy)carbonyl]amino]-4-methylpentyl]-L-Proline. The title compound of Example 1a (8.14 g) was dissolved in absolute ethanol (30 mL) and treated with #2-Raney nickel (60 mL 1:1 v/v slurry in absolute ethanol) at 22° C. for 2 hours. The reaction was filtered on a glass frit and washed with ethanol (700 mL).

The filtrate was concentrated under reduced pressure and chromatographed on silica gel to provide 1.05 g (18%) of the title compound and 835 mg (11%) of the 1-[2-(S)-[[(1,1-dimethylethoxy)carbonyl]amino]-4-methylpentyl]-L-Proline Benzyl ester. The $^1$H NMR of both these compounds were consistent with their structures.

c) 1-[2-(S)-[[(1,1-Dimethylethoxy)carbonyl]amino]-4-methylpentyl]-L-proline 4-phenylbutylamide. The title compound of Example 1b (392 mg), 1,3-dicyclohexylcarbodiimide (386 mg), dimethylaminopyridine (152 mg), 1-hydroxybenzotriazole monohydrate (191 mg) and triethylamine (350 uL) were dissolved in N,N-dimethylformamide (1 mL) and dichloromethane (2 mL) and were treated with 4-phenylbutylamine (296 uL). The reaction was stirred for 12 hours at 20° C., then concentrated under reduced pressure. The residue was dissolved in dichloromethane and washed with satd aq NaHCO$_3$, satd aq NaCl, dried (MgSO$_4$), and concentrated under reduced pressure to an oil. The oil was chromatographed on acidic silica gel to provide 356 mg (64%) of the title compound. The $^1$H NMR and Mass spectrum of this compound were consistent with the structure. Rf=0.26 (50% EtOAc in hexane). LSIMS=446; (mass calculated for C$_{26}$H$_{43}$N$_3$O$_3$=445.62).

d) 1-[2-(S)-Amino-4-methylpentyl]-L-proline 4-Phenylbutylamide. The title compound of Example 1c (455 mg) was dissolved in dichloromethane (3 mL) and treated with trifluoroacetic acid (3 mL). The reaction was stirred at 20° C. for 3 hours, then concentrated under reduced pressure. The residue was dissolved in dichloromethane and was washed with said aq NaHCO$_3$, said aq NACl, dried (MgSO$_4$), and concentrated under reduced pressure to provide 332 mg (94%) of the free amine. The $^1$H NMR of this compound was consistent with the structure, and the amine was used directly for subsequent reactions.

1e) 1-[2-(S)-Methanesulfonylamino-4-methylpentyl]-L-proline 4-Phenylbutylamide. In a round bottom flask were added 1-[2-(S)-amino-4-methylpentyl]-L-proline 4-phenylbutylamide (20 mg), triethylamine (20 uL) and anhydrous dichloromethane (1 mL). The solution was cooled to −78° C., and methane sulfonyl chloride (7 uL) was added. After the addition was complete, the solution was allowed to warm to 0° C. and then to 22° C. The reaction mixture was washed with said aq NaHCO$_3$, said aq NaCl, dried (MgSO$_4$), evaporated under reduced pressure, and chromatographed on silica to provide 11 mg (45%) of the title compound. The $^1$H NMR and Mass spectrum of this compound were consistent with the structure. Rf=0.38 (EtOAc). LSIMS=424; (mass calculated for C$_{22}$H$_{37}$N$_3$O$_3$S=423.60).

Example 2

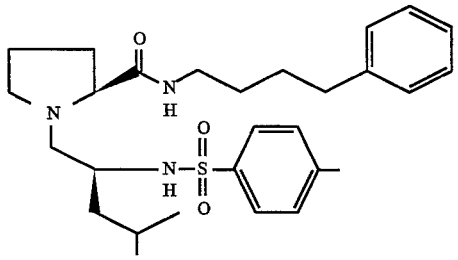

1-[2-(S)-(Toluene-4-sulfonylamino)-4-methylpentyl]-L-proline 4-Phenylbutylamide. Using the procedure described in Example 1e, treatment of 1-[2-(S)-amino-4-methylpentyl]-L-proline 4-phenylbutylamide (20 mg) with p-toluenesulfonyl chloride (16 mg) provided 13 mg (44%) of the title compound. The $^1$H NMR and Mass spectrum of this compound were consistent with the structure. Rf=0.54 (EtOAc). LSIMS=500; (mass calculated for C$_{28}$H$_{41}$N$_3$O$_3$S=499.69).

Example 3

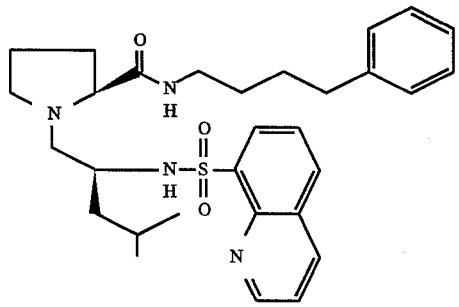

1-[2-(S)-(Quinoline-8-sulfonylamino)-4-methylpentyl]-L-proline 4-Phenylbutylamide. Using the procedure described in Example 1e, treatment of 1-[2-(S)-amino-4-methylpentyl]-L-proline 4-phenylbutylamide (40 mg) with 8-quinolinesulfonyl chloride (40 mg) provided 33 mg (54%) of the title compound. The $^1$H NMR and Mass spectrum of this compound were consistent with the structure. Rf=0.44 (EtOAc). LSIMS=537; (mass calculated for C$_{30}$H$_{40}$N$_4$O$_3$S=536.71).

Example 4

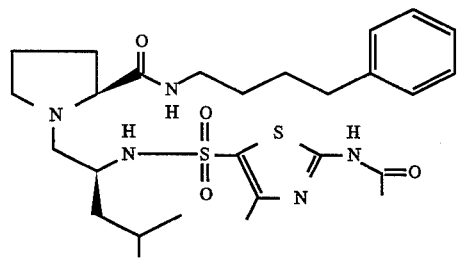

1-[2-(S)-(2-Acetylamino-4-methyl-S-thiazolesulfonylamino)-4-methylpentyl]-L-proline 4-Phenylbutylamide. Using the procedure described in Example 1e, treatment of 1-[2-(S)-amino-4-methylpentyl]-L-proline 4-phenylbutylamide (116 mg) with 2-acetamido-4-methyl-5-thiazolsulfonyl chloride (116 mg) provided 60 mg (35%) of the title compound. The $^1$H NMR and Mass spectrum analysis of this compound were consistent with the structure. Rf=0.49 (4.8% methanol in dichloromethane). LSIMS=564; (mass calculated for C$_{27}$H$_{41}$N$_5$O$_4$S$_2$=563.76).

Example 5

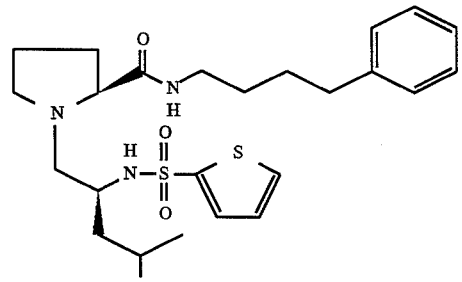

1-[2-(S)-(Thiophene-2-sulfonylamino)-4-methylpentyl]-L-proline 4-Phenylbutylamide. Using the procedure described in Example 1e, treatment of 1-[2-(S)-amino-4-methylpentyl]-L-proline 4-phenylbutylamide (115 mg) and 2-thiophenesulfonyl chloride (80 uL) provided 107 mg (75%) of the title compound. The $^1$H NMR and Mass spectrum of this compound were consistent with the structure. Rf=0.49 (4.8% methanol in dichloromethane). LSIMS=492; (mass calculated for $C_{25}H_{37}N_3O_3S_2$=491.69).

Example 6

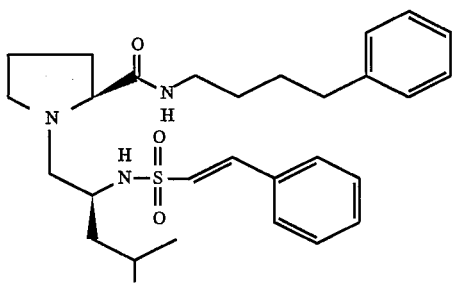

1-[2-(S)-(2-phenyl-ethenesulfonylamino)-4-methylpentyl]-L-proline 4-Phenylbutylamtde. Using the procedure described in Example 1e, treatment of 1-[2-(S)-amino-4-methylpentyl]-L-proline 4-phenylbutylamide (124 mg) with trans-betastyrenesulfonyl chloride (82 mg) provided 111 mg (67%) of the title compound. The $^1$H NMR and Mass spectrum of this compound were consistent with the structure. Rf=0.51 (EtOAc). LSIMS=512; (mass calculated for $C_{29}H_{41}N_3O_3S$=511.70).

Example 7

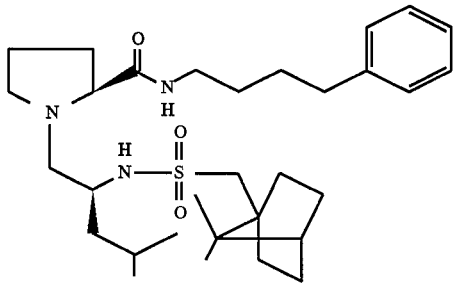

1-[2-(S)-(7,7-Dimethyl-2-oxo-bicyclo[2.2.1]hept-1-ylmethanesulfonylamino)-4-methylpentyl]-L-proline 4-Phenylbutylamide. Using the procedure described in Example 1e, treatment of 1-[2-(S)-amino-4-methylpentyl]-L-proline 4-phenylbutylamide (132 mg) with (-)-10-camphorsulfonyl chloride (108 mg) provided 99 mg (51%) of the title compound. The 1H NMR and Mass spectrum of this compound were consistent with the structure. Rf=0.56 (EtOAc). LSIMS=560; (mass calculated for $C_{31}H_{49}N_3O_4S$=559.78).

Example 8

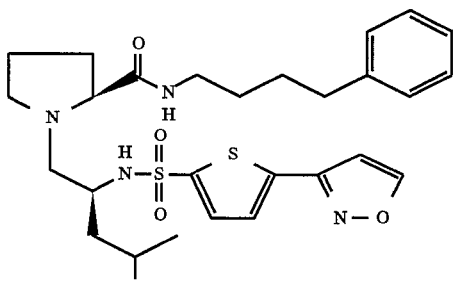

1-[2-(S)-(5 - [Isoxazol- 25 -yl]-thiophene-2 -sulfonylamino)-4-methylpentyl]-L-proline 4-Phenylbutylamide. Using the procedure described in Example 1e, treatment of 1-[2-(S)-amino-4-methylpentyl]-L-proline 4-phenylbutylamide (123 mg) with 5-(isoxazol-3-yl)thiophene-2-sulfonyl chloride (Maybridge Chemical: 125 mg) provided 24 mg (13%) of the title compound. The $^1$H NMR and Mass spectrum analysis of this compound were consistent with the structure. Rf=0.28 (3.2% methanol in dichloromethane). LSIMS=559; (mass calculated for $C_{28}H_{38}N_4O_4S_2$=558.73).

Example 9

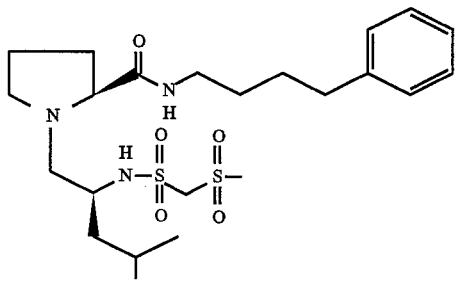

1-[2-(S)-(Methylsulfonylmethanesulfonylamino)-4-methylpentyl]-L-proline 4-Phenylbutylamide. Using the procedure described in Example 1e, treatment of 1-[2-(S)-amino-4-methylpentyl]-L-proline 4-phenylbutylamide (114 mg) with methylsulfonylmethylsulfonyl chloride (Maybridge Chemical: 103 mg) provided 38 mg (26%) of the title compound. The $^1$H NMR and Mass spectrum of this compound were consistent with the structure. Rf=0.56 (EtOAc). LSIMS=502; (mass calculated for $C_{23}H_{39}N_3O_5S_2$=501.68).

Example 10

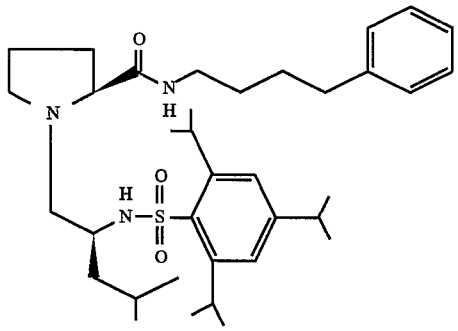

1-[2-(S)-(2',4',6'-Triisopropylbenzenesulfonylamino)-4-methylpentyl]-L-proline 4-Phenylbutylamide. Using the procedure described in Example 1e, treatment of 1-[2-(S)- amino-4-methylpentyl]-L-proline 4-phenylbutylamide (136 mg) with 2,4,6-triisopropylbenzenesulfonyl chloride (163 mg) provided 75 mg (34%) of the title compound. The $^1$H NMR and Mass spectrum of this compound were consistent with the structure. Rf=0.65 (EtOAc). LSIMS=632; (mass calculated for $C_{36}H_{57}N_3O_3S$=611.90).

Example 11

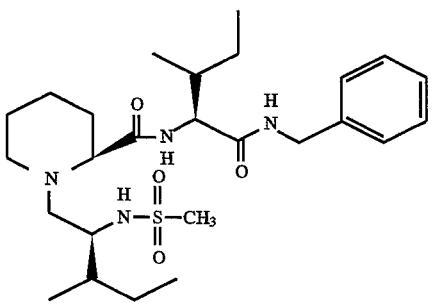

1-[1-[2-(S)-ethanesulfonylamino-3-(S)-methylpentyl]-L-homoprolyl]-L-isoleucine Benzylamide. Using the procedure described in Example 1e, 1-[2-(S)-amino-3-(S)-methylpentyl]-L-homopropyl]-L-isoleucine benzylamide (722 mg) was acylated at −78° C. with methane sulfonyl chloride (130 uL) to give 347 mg (41%) of the title compound. The $^1$H NMR and Mass spectrum of this compound were consistent with the structure. Rf=0.59 (EtOAc). LSIMS=509; (mass calculated for $C_{26}H_{44}N_4O_4S$=508.70).

The immunosuppressive properties of the present compounds were evaluated in the following assays:

1) Inhibition of PPIase Activity

This assay follows in principle the procedure described in Kofron et al., 1991, Biochemistry 30:6127. The three main reagents used are PPIase, a substrate for PPIase, and a selected inhibitor compound of the present invention. The basic principle behind this assay is the conversion of the cis isomer of the substrate to the trans form, which conversion is catalyzed by PPIase. Essentially, inhibition of this PPIase activity is measured for the selected compounds. A peptide chymotrypsin substrate containing a proline in the P2 position is only cleaved by chymotrypsin when the Phe-Pro bond is in the trans isomeric configuration. In the presence of excess chymotrypsin, all of the trans peptide isomers are cleaved within approximately five seconds, leaving only cis forms.

The cis peptide will spontaneously convert to the trans isomer at a slow rate. The cis to trans conversion is catalyzed by isomerases at a much faster rate than this spontaneous conversion. Proteins with PPIase activity are examples of such isomerases. After isomerization, the peptide is cleaved by chymotrypsin releasing p-nitroaniline which can be monitored at 390 nm. The rate of release is then calculated using a first order rate plus offset equation utilizing the ENZFITTER program (Leatherbarrow, BIOSOFT, Cambridge, United Kingdom).

Example 12

PPIase Inhibition Assay

In a plastic cuvette are added 950 ul of ice cold assay buffer (25 mM HEPES, pH 7.8, 100 mM NaCl), 10 uL of FKBP (2.5 uM in 10 mM Tris-Cl pH 7.5,100 mM NACl, 1 mM dithiothreitol), 25 ul of chymotrypsin (50 mg/ml in 1 mM HCl) and 10 ul of the test compound at various concentrations in dimethyl sulphoxide. The reaction is initiated by addition of 5 ul of substrate (Succinyl-Ala-Phe-Pro-Phe-para-nitroanilide, 5 mg/ml in 235 mM LiCl in trifluoroethanol).

The absorbance at 390 nm versus time is monitored for 90 sec using a Beckman DU70 spectrophotometer. The absorbance versus time data files are transferred to an IBM XT computer and the rate constants determined using the commercial Enzfitter program. For each set of data, the uncatalyzed rate of conversion is measured and the uninhibited enzymatic rate determined. The data are expressed as % Inhibition and are calculated as follows:

$$\% \text{ Inhibition} = \left[ 1 - \frac{(k_{obs} - k_{uncat})}{(k_{uninh} - k_{uncat})} \right] \times 100$$

where $k_{obs}$ is the rate in the presence of a selected test compound, $k_{uncat}$ is the rate in the absence of enzyme, and $k_{uninh}$ is the rate in the presence of enzyme and absence of inhibitor. Data are plotted as percent inhibition versus concentration of inhibitor. The values of the concentration of inhibitor required for 50% inhibition of enzyme activity ($IC_{50}$) were determined by nonlinear least squares regression analysis.

TABLE 1

| Example No. | FKBP $IC_{50}$ (μM) |
| --- | --- |
| 1 | 3.5 |
| 2 | >5 |
| 3 | >5 |
| 4 | >5 |
| 5 | >5 |
| 6 | >5 |
| 7 | >5 |
| 8 | >5 |
| 9 | >5 |
| 10 | >5 |
| 11 | >5 |

Results: The results of the compound testing are presented in Table 1, above. As stated previously, it was not initially apparent whether or not inhibition of PPIase activity was necessary and sufficient for immunosuppression. Presently, the prevailing thought is that binding to the PPIase enzyme may be necessary but is not sufficient. Therefore, the data on PPIase inhibition may be viewed as an assay to detect whether or not a given compound is capable of interacting productively with FKBP.

2) Human T Lymphocyte Inhibition

Inhibition of mitogen-induced T-cell proliferation can be used to profile immunosuppressive activity of test compounds. In the description of the assay which follows, mitogen-induced T-cell proliferation was used to test the inhibitory potencies of select compounds of the present invention.

In an assay similar to that described by Bradley in Mishell et al. (Eds.), 1980, Selected Methods in Cellular Immunology, pp 156–161, W. H. Freeman & Co., San Fransisco, Calif., T-cells were stimulated by incubation with phytohemagglutinin (PPIA) which binds to cell surface molecules, including the T-cell receptor. This stimulation results in proliferation which can be measured by incorporation of [$^3$H]-thymidine into cellular DNA.

The immunosuppressive properties of the compounds of the present invention can be determined by adding various concentrations of the compounds to these cultures and measuring the effect on T-cell proliferation.

Example 13

Suppression of Human T-Cell Proliferation Assay

Fresh LeukoPaks were obtained from the New York Blood Center, New York, N.Y. The cells, including erythrocytes and leukocytes, were diluted with Hank's Balanced Salt Solution (HBSS) (GIBCO, Grand Island, N.Y.) and layered over Lymphoprep (Nycomed Pharma AS, Oslo, Norway) in sterile 50 ml conical centrifuge tubes. Lymphocytes were isolated at the Hank's/Nycomed interface after centrifugation at 2000×g, 4° C. for 15 min. The lymphocytes were washed with Minimal Essential Medium (GIBCO) containing 2% fetal bovine serum (FBS) (Sigma Chemical Co., St. Louis, Mo.), 1% HEPES buffer (GIBCO) and 1% Penicillin-Stretomycin solution (GIBCO).

T-cells were further purified essentially by sheep erythrocyte (SRBC) rosetting as described by Morimoto et al., 1983, J. Immunol. 130:157. The isolated lymphocytes were adjusted to $2 \times 10^7$ cells/ml and 5 ml aliquots of the cell suspension were incubated for 10 minutes at room temperature with 5 ml of a 5% SRBC (Cappel, Organon Technika Corp., West Chester, Pa.) suspension. The cells were gently pelleted by centrifugation at 300 rpm for 10 minutes, followed by a 1 hour incubation at room temperature to allow rosette formation. The cells were gently resuspended, layered over Lymphoprep and centrifuged for 30 minutes at 500×g. The pellet, containing rosetted T-cells and SRBC was treated with ice cold buffered ammonium chloride (GIBCO) to lyse the erythrocytes. T-cells were washed twice with HBSS.

Purified T-cells were resuspended at $2 \times 10^6$ cells/ml in complete culture medium composed of RPMI-1640 (Whittaker Bioproducts, Walkerville, Md.) with 10% FBS (Sigma), 2 mM L-glutamine (GIBCO), 1% Penicillin-Streptomycin (GIBCO) and 15 mM HEPES (GIBCO). In 96-well plates (Becton Dickinson, Lincoln Park, N.J.), 0.1 ml aliquots of T-cell suspension were mixed with 0.05 ml of 40 µg/ml PPIA-M (Sigma). The compounds of this invention were dissolved in dimethylsulfoxide at 10 mM and various dilutions in complete medium were added in duplicate wells (0.05 ml/well). The plates were incubated at 37° C. in a humidified atmosphere of 5% carbon dioxide and 95% air for 72 hours.

Proliferation was assessed by measurement of [3H]-thymidine incorporation. During the last 6 hours of incubation, the cells were pulse labelled with 1 µCi/well of [3H]-thymidine (New England Nuclear, Boston, Mass.). The cells were harvested onto glass fiber paper using a plate harvester and the radioactivity incorporated into cellular DNA corresponding to individual wells was measured by standard liquid scintillation counting methods. The mean counts per minute (CPM) of replicate wells was calculated and linear regression analysis of mean CPM versus compound concentration was used to determine the concentration of compound which would inhibit [$^3$H]-thymidine incorporation of T-cells by 50% ($IC_{50}$).

The results of this assay, presented in Table 2, are representative of the intrinsic immunosuppresive activity of the compounds of the present invention. Thus, concentrations less than 10 µM of some of the preferred compounds suppress the T-cell proliferative response by 50%.

TABLE 2

| Example No. | $IC_{50}$ (µM) |
| --- | --- |
| 1 | 2 |
| 2 | 8 |
| 3 | 5 |
| 4 | 2 |
| 5 | 3 |
| 6 | 5 |
| 7 | 2 |
| 8 | 1 |
| 9 | 4 |
| 10 | 4 |
| 11 | >15 |

3) NF-AT Assay

Stimulation of T-cells leads to the appearance of several transcription factors, including one designated "NF-AT". These factors are involved in regulation of gene expression required for immunologic activation. Some of these transcription factors appear to have functions in a wide variety of cell types. By contrast, NF-AT is found primarily in T-cells and its role is restricted to early gene activation. In addition, NF-AT activity is inhibited by the immunosuppressant drugs, Cyclosporin A and FK506 (Schreiber and Crabtree, 1992, Immunology Today 13:136).

Inhibition of NF-AT activity is measured using FGL-5 cells. FGL-5 is a cloned line of stably transfected Jurkat T-cells that contain a construct in which three tandem copies of the NF-AT DNA binding site direct transcription of the lacZ gene, encoding β-galactosidase (Fiering et al., 1990, Genes & Development 4:1823). When these cells are stimulated with phorbol esters which activate protein kinase C and calcium ionophore to raise the intracellular calcium concentration, transcriptionally active NF-AT is produced. In T-cells, this normally leads to the expression of IL-2, T-cell growth factor. However, in FGL-5 cells NF-AT activation leads to the production of β-galactosidase which can be detected using an appropriate substrate.

FGL-5 cells were cultured with phorbol ester, calcium ionophore and the compounds of the present invention to measure inhibition of β-galactosidase activity, as shown below.

Example 14

NF-AT Inhibition Assay Directed β-Galactosidase Expression

This assay was performed essentially as described (Bierer et al., 1990, Proc. Natl. Acad. Sci. 87:9231). FGL-5 cells were maintained in medium consisting of RPMI-1640 with 10% FBS, 2 mM L-glutamine, 1% Penicillin- Streptomycin and 15 mM HEPES buffer. The assays were done with exponentially growing cells whose density was not greater than 0.5 million cells/ml. The cells were resuspended to 3 million cells/ml in medium and 0. 1 mi was added to wells of a 96-well plate.

The compounds of the present invention were dissolved in either ethanol or dimethylsulfoxide at 10 mM and 0.05 ml/well of various dilutions in medium were added to cells in duplicate wells. Treatment controls consisted of duplicate wells to which 0.05 ml/well of either medium, ethanol or dimethylsulfoxide was added. The ethanol and dimethyl sulfoxide were at the same concentration as was used for the compounds. Cells were incubated with compounds at room temperature for 10–15 minutes. Phorbol dibutyrate (Sigma) and Ionomycin (Calbiochem) were dissolved at 50 µg g/mi and 2 mM, respectively and stored at –70° C.

FGL-5 cells were stimulated by diluting these reagents with medium to 200 ng/ml and 8 µM, respectively and adding of 0.05 ml/well. For unstimulated cell controls, 0.05 ml/well of medium was added to duplicate wells. The plates were incubated overnight (16–18 hours) at 37° C. in a humidified atmosphere of 5% $CO_2$ and air. β-galactosidase activity was measured as the fluorescence generated by the cleavage of 4-methyl umbelliferyl-β-D-galactoside (Sigma) at the β-galactoside bond. After overnight incubation, the cells were centrifuged at 500×g for 3 minutes in the 96-well plates and washed 3 times with PBS. The cells were then resuspended in 0. 18 mi/well of reaction medium containing 100 mM sodium phosphate buffer, pH 7.0, 10 mM potassium chloride, 1 mM magnesium sulfate, 0.1% Triton X-100 (Pierce, Rockford, Ill.), and 0.5 mM 4-methylumbelliferyl-β-D- galactoside.

The fluorescence at 460 nm using 355 nm excitation was measured at intervals over 1–2 hours (during which fluorescence increased linearly with time) with a LS50 Luminescence Spectrometer (Perkin Elmer).

The percent inhibition by each concentration of the compounds was calculated as:

% Inhibition =

$$1 - \frac{\text{(fluorescence with compound} - \text{unstimulated control)}}{\text{(fluorescence with solvent alone} - \text{unstimulated control)}} \times 100$$

The values of the concentration of compounds required for 50% inhibition ($IC_{50}$) were determined by linear regression analysis of the percent inhibition at various compound concentrations.

The results of this assay presented in Table 3 are representative of the intrinsic immunosuppresive activity of the compounds of the present invention. Compounds that inhibited NF-AT directed β-galactosidase expression by stimulated FGL-5 cells with $IC_{50}$ of 11 µM or less also inhibited mitogen induced T-cell proliferation, e.g., compounds of Example Nos. 1 and 3.

TABLE 3

| Example No. | $IC_{50}$ (µM) |
|---|---|
| 1 | 9 |
| 2 | 27 |
| 3 | 11 |
| 4 | 24 |
| 5 | 24 |
| 6 | >15 |
| 7 | >15 |
| 8 | >15 |
| 9 | ND |
| 10 | >15 |
| 11 | >15 | where ND means "not determined"

4) Adjuvant Arthritis

Rats sensitized to mycobacterial antigens in Complete Freund's Adjuvant can develop a rapidly destructive adjuvant arthritis. Adjuvant arthritis appears to be an autoimmune disease. Thus, T lymphocytes from immunized donors can transfer the disease to naive recipients (Pearson and Wood, 1964, J. Exp. Med. 120:547.) and susceptibility is controlled, at least in part, by class II MHC genes (Batisto, et al. 1982, Arthritis Rheum. 25:1194). The induction of adjuvant arthritis can be inhibited by immunosuppressant drugs, e.g., Cyclosporin A (Borel, et al., 1976, Agents and Actions. 6:468) and azaspiranes (Badger, et al. 1989, Int. J. Immunopharmac. 11:839)

Example 15

Adjuvant Arthritis Model in the Rat

Complete Freund's adjuvant is made by supplementing extra heavy mineral oil with 10 mg/ml heat killed *Mycobacterium butyricum* (Difco Laboratories, Detroit, Mich.). Lewis rats (Charles Rivers, Willmington, Mass.) are given a 0. 1 ml injection of adjuvant (1 mg/animal mycobacterium) subcutaneously into the right hind footpad. In the injected foot, an acute inflammatory reaction occurs which is characterized by erythema, edema and a predominantly neutrophilic cell infiltrate. This is followed by edema in the uninjected contralateral foot by days 10–12. This secondary response is accompanied by a predominantly mononuclear cell infiltrate, indicating the presence of cell-mediated immunity.

The immune response is quantitated by measuring the change in ankle diameter of the uninjected hind paw from day 0 to day 16 post sensitization. This is accomplished using a hand-held dial micrometer. Animals are administered test drugs, suspended in a vehicle consisting of 5% polyethylene glycol and 0.5% Tween-80 (Sigma Chemical Co., St. Louis, Mi,) in phosphate buffered saline (GIBCO, Grand Island, N.Y.), i.p. on days −1, 0, 2, S, 7, 9, 12 and 14. Several compounds when administered at 10 mg/kg/dose inhibited the swelling in the uninjected limb compared with the control groups that were sensitized with Complete Freund's Adjuvant but received only the vehicle i.p. (Table 4).

TABLE 4

| Compound | Δ Ankle Diameter | % Inhibition |
|---|---|---|
| None | 3.3 ± 0.5 mm | 0 |
| Example 1 | 1.6 ± 0.6 mm | 51 |

What is claimed is:

1. A compound having the structure:

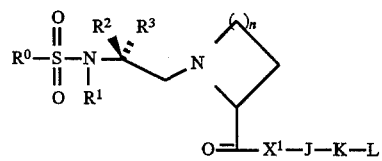

where $R^0$ is straight or branched ($C_1$–$C_{10}$)alkyl, ($C_3$–$C_{10}$) cycloalkyl, ($C_5$–$C_{12}$)bicycloalkyl, or ($C_7$–$C_{14}$) tricycloalkyl, each of which is optionally substituted with a straight or branched ($C_1$–$C_3$)alkoxy, cyano, straight or branched carbo($C_1$–$C_6$)alkoxy, ($C_1$–$C_5$) alkylsulfonyl, one to three fluoro groups, or with a doubly bonded oxygen atom to form a ketone; or $R^0$ is styryl, or a phenyl group optionally substituted up to three times with a straight or branched ($C_1$–$C_6$)alkyl;

$R^1$ is hydrogen or methyl;

one of $R^2$ and $R^3$ is hydrogen and the other is straight or branched ($C_1$–$C_6$)alkyl optionally substituted with $C_6$ cycloalkyl, hydroxy, straight or branched ($C_1$–$C_4$) alkoxy, benzyloxy, or aryl optionally substituted with hydroxy or methoxy;

n is the integer 2;

$X^1$ is $NR^4$, where $R^4$ is hydrogen or methyl;

J is the divalent fragment $$-\underset{H}{\overset{R^5}{\underset{|}{C}}}-$$

where $R^5$ is hydrogen, or straight or branched ($C_1$-$C_8$)alkyl optionally substituted with hydroxy, straight or branched ($C_1$-$C_6$)alkoxy, benzyloxy, $C_6$ cycloalkyl or phenyl;

K is one of the fragments
—HC=CH— or —(CH$_2$)$_p$—
where;

p is the integer 1, 2, 3 or 4; and

L is hydrogen, phenyl, or straight or branched ($C_1$-$C_8$) alkyl optionally substituted with phenyl optionally substituted by straight or branched ($C_1$-$C_5$)alkoxy, hydroxy, or amino, which amino is optionally substituted by a straight or branched ($C_1$-$C_6$)alkyl, acetyl, or both.

2. A compound having the structure:

$$R^0-\underset{\underset{O}{\|}}{\overset{\overset{O}{\|}}{S}}-\underset{R^1}{\overset{R^2}{\underset{|}{N}}}\overset{R^3}{\diagdown}\text{N}\diagup(\diagdown)_n$$
$$O=\text{X}^1-\text{J}-\text{K}-\text{L}$$

where $R^0$ is straight or branched ($C_1$-$C_8$)alkyl, ($C_3$-$C_8$) cycloalkyl, ($C_5$-$C_{10}$)bicycloalkyl, or ($C_7$-$C_{12}$) tricycloalkyl, each of which is optionally substituted with a fluoro, methoxy, cyano, straight or branched carbo($C_1$-$C_4$)alkoxy, ($C_1$-$C_4$)alkylsulfonyl or with doubly bonded oxygen to form a ketone; or $R^0$ is styryl, or a phenyl group optionally substituted up to three times by straight or branched ($C_1$-$C_6$)alkyl;

$R^1$ is hydrogen or methyl;

one of $R^2$ and $R^3$ is hydrogen and the other is straight or branched ($C_1$-$C_6$) alkyl optionally substituted by $C_6$ cycloalkyl or phenyl;

n is the integer 2;

$X^1$ is $NR^4$, where $R^4$ is hydrogen or methyl;

J is the divalent fragment $$-\underset{H}{\overset{R^5}{\underset{|}{C}}}-$$

where $R^5$ is hydrogen or straight or branched ($C_1$-$C_6$)alkyl optionally substituted with hydroxy, straight or branched ($C_1$-$C_6$)alkoxy, benzyloxy, $C_6$ cycloalkyl, or phenyl;

K is one of the fragments
—HC=CH— or —(CH$_2$)$_p$—
where p is the integer 2 or 3: and L is hydrogen, phenyl, or straight or branched ($C_1$-$C_6$) alkyl optionally substituted with phenyl optionally substituted with ($C_1$-$C_5$)alkoxy, hydroxy, or amino, which amino is optionally substituted by ($C_1$-$C_4$)alkyl, or acetyl, or both.

3. A compound having the structure:

$$R^0-\underset{\underset{O}{\|}}{\overset{\overset{O}{\|}}{S}}-\underset{R^1}{\overset{R^2}{\underset{|}{N}}}\overset{R^3}{\diagdown}\text{N}\diagup(\diagdown)_n$$
$$O=\text{X}^1-\text{J}-\text{K}-\text{L}$$

where $R^0$ is straight or branched ($C_1$-$C_6$)alkyl optionally substituted with methylsulfonyl; or $R^0$ is styryl or a $C_{10}$ tricycloalkyl substituted by a doubly bonded oxygen to form a ketone; or $R^0$ is phenyl optionally substituted up to three times by straight or branched ($C_1$-$C_3$) alkyl;

$R^1$ is hydrogen;

one of $R^2$ and $R^3$ is hydrogen and the other is straight or branched ($C_1$-$C_4$)alkyl optionally substituted by $C_6$ cycloalkyl;

n is the integer 2;

$X^1$ is NH;

J is the divalent fragment $$-\underset{H}{\overset{R^5}{\underset{|}{C}}}-$$

where $R^5$ is hydrogen or straight or branched ($C_1$-$C_4$)alkyl;

K is one of the fragments
—HC=CH— or —(CH$_2$)$_p$—
where p is the integer 2; and L is hydrogen, phenyl, or straight or branched ($C_1$-$C_3$) alkyl optionally substituted by aryl.

4. A therapeutic composition for suppressing the proliferation of human T-lymphocytes, comprising an effective amount of a compound according to claim 1.

5. A therapeutic composition for suppressing the proliferation of human T-lymphocytes, comprising an effective amount of a compound according to claim 2.

6. A therapeutic composition for suppressing the proliferation of human T-lymphocytes, comprising an effective amount of a compound according to claim 3.

7. The compound of claim 3 named 1-[2-(S)-Methanesulfonylamino-4-methylpentyl]-L-proline 4-Phenylbutylamide.

8. The compound of claim 3 named 1-[2-(S)-Toluene-4-sulfonylamino)-4-methylpentyl]-L-proline 4-Phenylbutylamide.

9. The compound of claim 3 named 1-[2-(S)-(2-phenylethenesulfonylamino)-4-methylpentyl]-L-proline 4-Phenylbutylamide.

10. The compound of claim 3 named 1-[2-(S)-(7,7-Dimethyl-2-oxobicyclo[2.2.1]hept-1-ylmethanesulfonylamino)-4-methylpentyl]-L-proline 4-Phenylbutylamide.

11. The compound of claim 3 named 1-[2-(S)-(Methylsulfonylmethanesulfonylamino)-4-methylpentyl]-L-proline 4-Phenylbutylamide.

12. The compound of claim 3 named 1-[2-(S)-(2',4',6'-Triisopropylbenzenesulfonylamino)-4-methylpentyl]-L-proline 4-Phenylbutylamide.

* * * * *